US010143938B2

(12) United States Patent
Akula et al.

(10) Patent No.: US 10,143,938 B2
(45) Date of Patent: Dec. 4, 2018

(54) PROCESS FOR PURIFICATION AND ISOLATION OF ESTROGENS

(71) Applicant: Dr. Reddy's Laboratories Ltd., Hyderabad (IN)

(72) Inventors: Chandrashaker Akula, Middleburgh, NY (US); John Lomans, Middleburgh, NY (US); Madhukiran Tummidi, Middleburgh, NY (US); Prashant Anil Tatake, Mumbai (IN)

(73) Assignee: DR. REDDY'S LABORATORIES LTD., Hyderabad (IN)

( * ) Notice: Subject to any disclaimer, the term of this patent is extended or adjusted under 35 U.S.C. 154(b) by 50 days.

(21) Appl. No.: 15/262,570

(22) Filed: Sep. 12, 2016

(65) Prior Publication Data

US 2016/0375378 A1    Dec. 29, 2016

Related U.S. Application Data

(63) Continuation of application No. 14/304,188, filed on Jun. 13, 2014.

(60) Provisional application No. 61/835,032, filed on Jun. 14, 2013.

(51) Int. Cl.
| | | |
|---|---|---|
| *B01D 15/36* | (2006.01) | |
| *A61K 31/566* | (2006.01) | |
| *B01J 20/26* | (2006.01) | |
| *B01D 15/38* | (2006.01) | |
| *A61K 31/565* | (2006.01) | |

(52) U.S. Cl.
CPC .......... *B01D 15/362* (2013.01); *A61K 31/565* (2013.01); *A61K 31/566* (2013.01); *B01D 15/361* (2013.01); *B01D 15/363* (2013.01); *B01D 15/3828* (2013.01); *B01J 20/261* (2013.01)

(58) Field of Classification Search
None
See application file for complete search history.

(56) References Cited

U.S. PATENT DOCUMENTS

| | | | |
|---|---|---|---|
| 2,551,205 A | 5/1951 | Cook et al. | |
| 2,696,265 A | 12/1954 | Beall et al. | |
| 2,711,988 A | 6/1955 | Deans et al. | |
| 2,834,712 A | 5/1958 | Beall et al. | |
| 5,814,624 A | 9/1998 | Ban et al. | |
| 7,439,235 B2 | 10/2008 | Heinz-Helmer et al. | |
| 8,349,819 B2 | 1/2013 | Lomans et al. | |
| 2005/0032767 A1* | 2/2005 | Heinz-Helmer | C07J 75/00 514/182 |
| 2009/0312293 A1 | 12/2009 | Mazzola et al. | |
| 2011/0040095 A1* | 2/2011 | Bollikonda | C07D 215/18 546/174 |

FOREIGN PATENT DOCUMENTS

CA    2263757 C    3/1998

OTHER PUBLICATIONS

Krol et al. In Recent Progress in Hormone Research, vol. V, G. Pincus Ed. Academic Press, N.Y. 1950.*
Sephadex LH-20 in https://openi.nlm.nih.gov/detailedresult.php?img= PMC3515891_ISRN.PHARMACEUTICS2012-216068.001 &req=4 (retrieved from the internet May 6, 2016).*
Fritz et al. in Clinical Gynecologic Endocrinology and Infertility, Eighth Edition, Lippincott Williams and Wilkins, 2011, 2005.*
Grant et al. In Recent Progress in Hormone Research, vol. V, G. Pincus Ed. Academic Press, N.Y. 1950.*
Filters FAQ Alumina in www.friendsofwater.com/filters-faq/ (retrieved from the internet May 6, 2016).*
Bain et al. in Steroids 43(6):603-609 (1984) (Abstract).*
Synthetic Adsorbents' at www.dormeco.co.il/wp-content/uploads/2012/10/Sepabeads-%E2%80%93-Synthetic-Adsorbents.pdf)) (retrieved from the internet May 6, 2016).*
Non-Final Office Action dated May 17, 2016, mailed by the USPTO, for corresponding U.S. Appl. No. 14/304,188.
Krol et al., "Quantitative Separation of Free Estrogens by Liquid Partition Chromatography", Oct. 1970, pp. 1483 to 1487, vol. 59—issue No. 10.
Filters FAQ Alumina in www.friendsofwater.com/filters-faq/ (retrieved on May 6, 2016), pp. 1 to 11.
Sephadex LH-20 in https://openi.nlm.nih.gov/detailedresult.php?img=PMC3515891_ISRN_PHARMACEUTICS2012-216068.001 &req=4 (retrieved on May 6, 2016), pp. 1 to 2.
Gordon A Grant and Desmond Beall, "Studies on Estrogen Conjugates", Recent Progress in Hormone Research, 1950, pp. 307 to 327, Academic Press, Inc., Publishers, New York, NY.
Marc A. Fritz and Leon Speroff, Clinical Gynecologic Endocrinology and Infertility, Eighth Edition, Lippincott Williams & Wilkins, 2011, 2005.
Abstract of Bain et al., Jun. 1984, pp. 603 to 619, vol. 43—issue No. 6.
Synthetic Absorbents at www.dormeco.co.il/wp-contents/uploads/2012/10/Sepheads/-%E2%80%93-Synthetic-Absorbents.pdf.

* cited by examiner

*Primary Examiner* — Dennis Heyer
(74) *Attorney, Agent, or Firm* — Pergament & Cepeda LLP; Milagros A. Cepeda; Edward D. Pergament

(57) ABSTRACT

The present application relates to a method for obtaining a mixture of estrogens from the pregnant mare's urine.

17 Claims, No Drawings

PROCESS FOR PURIFICATION AND ISOLATION OF ESTROGENS

This application is a Continuation of U.S. patent application Ser. No. 14/304,188, filed on Jun. 13, 2014, which claims the benefit of U.S. Provisional Application No. 61/835,032, filed Jun. 14, 2013, all of which are hereby incorporated by reference in their entireties.

INTRODUCTION

The present application relates to a method for obtaining a mixture of estrogens from the pregnant mare's urine (PMU).

BACKGROUND

Estrogens are used in medicine for hormone replacement therapy. In particular, estrogen mixtures are used for the treatment and prophylaxis of the disorders of the climacteric period which occur in women after natural or artificial menopause. The mixtures of estrogens such as those found in the urine of pregnant mares are proved to be particularly effective and readily compatible for treatment of such disorders.

Mixture of estrogens include conjugated estrogens salts comprising estrone, equilin, $\Delta^{8,9}$-dehydroestrone, 17α-estradiol; 17α-dihydroequilin, 17α-dihydroequilin, 17α-estradiol, equilenin, 17α-dihydroequilenin; 17β-dihydroequilenin and optionally also one or more conjugated salts from the group of 17β-$\Delta^{8,9}$-dehydroestradiol; 17α-$\Delta^{8,9}$-dehydroestradiol; 6-OH 17α-dihydroequilenin; 6-OH equilenin; 6-OH 17β-dihydroequilenin and/or other sulphated steroidal metabolites. Salts are preferably sodium salts, while conjugated are mainly sulfates.

The amount of estrogens present in the pregnant mare's urine (PMU) may vary largely between the lots. PMU generally contains urea, steroids including estrogens, phenolic constituents which include cresols and dihydro-3,4-bis[(3hydroxyphenyl) methyl]-2(3H)-furanone (HPMF) and other urinary impurities.

The U.S. Pat. No. 2,551,205; U.S. Pat. No. 2,696,265; U.S. Pat. No. 2,711,988 and U.S. Pat. No. 2,834,712 disclose process for the isolation of a mixture of estrogens from pregnant mare's urine by liquid-liquid extraction method. Such liquid-liquid extraction methods have accompanying problems such as severe foaming, sedimentation, emulsification and poor phase separation, which generates large amounts of hazardous waste and therefore are difficult to practice at the commercial scale.

U.S. Pat. No. 5,814,624 discloses a method for obtaining a mixture of conjugated estrogens from pregnant mare's urine comprising adsorption of mixture of estrogens from PMU on a resin and eluting estrogens-loaded resin with an aqueous buffer solution.

U.S. Pat. No. 7,439,235 discloses a method for obtaining a mixture of conjugated estrogens, depleted in phenolic constituents, from pregnant mare's urine comprising adsorption of mixture of conjugated estrogens from PMU on a resin and eluting conjugated estrogens loaded resin with aqueous alkaline solution. The aqueous alkaline solution eluate is expected to remove the phenolic constituents and the mixture of conjugated estrogens was isolated from the fractions containing the desired amount of the product.

U.S. publication No. 2009/0312293 A1 discloses a similar process wherein the resin used for adsorption of mixture of conjugated estrogens from PMU is porous styrene-divinyl benzene polymer brominated at the styrene and/or divinylbenzene portion, with 600 m²/g area, 1.3 ml/g volume (dry weight), about 200 Angstrom pore size and eluting the estrogens from the resin with water: water-miscible solvent.

Canadian patent CA 2263757 discloses a method for isolation of a mixture of conjugated estrogens, depleted in phenolic urine contents, from pregnant mare's urine by using water miscible organic solvent or a mixture of water miscible organic solvent and water which has optionally been rendered alkaline.

The reported procedures involve usage of water alone or in combination with other solvents optionally in alkaline condition as an elution liquid for the purpose of purification and/or isolation of estrogens from the resin loaded with estrogens.

U.S. Pat. No. 8,349,819 discloses a method for purification and isolation of a mixture of estrogens involving the usage of multiple resins, which makes the process less economic.

There remains a need to provide an improved purification and isolation method for obtaining a mixture of estrogens from pregnant mare's urine which is simple, economic and industrially viable, which avoids usage of multiple resins and tedious isolation methods.

SUMMARY

In an aspect, the present application provides a method for obtaining a mixture of estrogens from pregnant mare's urine, comprising:
a) adsorbing a mixture of estrogens from pregnant mare's urine on a resin;
b) washing the resin loaded with the mixture of estrogens with water immiscible organic solvent;
c) isolating the mixture of estrogens from the resin loaded with the mixture of estrogens.

DETAILED DESCRIPTION

In an aspect, the present application provides a method for obtaining a mixture of estrogens from pregnant mare's urine, comprising:
a) adsorbing a mixture of estrogens from pregnant mare's urine on a resin;
b) washing the resin loaded with the mixture of estrogens with water immiscible organic solvent;
c) isolating the mixture of estrogens from the resin loaded with the mixture of estrogens.

Step (a) involves adsorbing a mixture of estrogens from pregnant mare's urine on a resin.

PMU containing mixture of estrogens used in step (a) includes urine directly collected from the pregnant mares or the PMU obtained after removal of the unwanted components such as salts or sediments from the directly obtained PMU. Suitable methods that are used to remove unwanted components from the directly collected urine of pregnant mares include, decantation and/or filtration at a temperature of less than about 30° C., less than about 20° C., less than about 15° C., less than about 10° C., less than about 5° C., less than about 0° C. or any suitable temperature.

Adsorbing a mixture of estrogens from pregnant mare's urine on a resin in step (a) includes percolating PMU containing mixture of estrogens through resin loaded in a column or by contacting PMU containing mixture of estrogens with a resin in a batch mode. The resulting PMU obtained after said percolation may be optionally re-circulated for one or more times or can be done without re-circulation that is washing by single passage of solvent through resin column. This circulation of urine is continued till the substantial amounts of conjugated estrogens present in the PMU are adsorbed on the resin. The time period for said percolation and/or said re-circulation depends upon the batch size and type of resin. Generally the time period may vary from few minutes to several weeks or any other suitable time period. For example the time period may be from about 10 minutes to about 6 weeks. The urine thus obtained after one or more circulations depleted substantially in the content of conjugated estrogens is discarded.

Suitable temperature that may be used in step (a) may be less than about 40° C., less than about 30° C., less than about 25° C., less than about 20° C., less than about 15° C., less than about 10° C., less than about 5° C., less than about 0° C. or any other suitable temperature.

Suitable resins that can be used in step (a) for adsorption of estrogens from pregnant mare's urine on a resin include ion exchange resins selected from cation exchange resins and anion exchange resins, chelated resins, synthetic adsorbents, non-ionic resins or combinations thereof. The resins may be lipophilic, hydrophilic and/or hydrophobic in nature.

Suitable resins that can be used for said adsorption in step (a) include RELITE™ EXL 04 (Commercially available from Mitsubishi), resins available from Itochu: Diaion PK208, PK212, PK216, PK220, PK228, UPK228, SK1B, SK1BH, SK104, SK110, SK112, SK116, RCP21H, RCP23H, RCP160M, RC11H, RC02H, RCP11H, RCP12H, RCP13H, UBK510L, UBK530, UBK535L, UBK550, UBK555, HPK25, Relite EXC04 (each having a polystyrene backbone and a sulfate pendant group); Diaion CR11 (having a polystyrene backbone and N,N-di(sodiumcarboxymethyl)aminomethyl pendent groups); CRP200 (having a polystyrene backbone and phosphatomethyl pendent groups); Diaion WK10, WK10S, WK11, WKI00, WT 01S (being polymethacrylic acid); Diaion WK40 (being polyacrylic acid); resins containing polymeric backbones selected from the group consisting of polystyrene-divinylbenzene, polyacrylate, polymethacrylate, poly(acrylate/methacrylate), polyacrylamide, polyphenolics and copolymers thereof where such backbones have side chains that include one or more of the aforementioned weakly anionic exchange groups. A highly preferred embodiment utilizes a polystyrene-divinylbenzene resin that is approximately 12% cross-linked and has tertiary ammonium side chains (maintained in the free form), which resin is commercially available under the name Dowex® XAD2 (available from DOW). Other weakly anionic exchange resins suitable for use in the present invention include, but are not limited to, those available from Itochu such as for example: Diaion SA10A. SA11A, SA12A, NSA100, SAF12A, HPA 25, PA 306S, PA308, PA312, and PA316 (each being a polystyrene backbone having a trimethylammoniummethyl side chain with a chloride counterion); Diaion SAF12 OH (being a polystyrene backbone having a trimethylammoniummethyl side chain with a hydroxide counterion); Diaion SA20A, SA21A, HPA75, PAF418, PA408, PA412, and PA418 (each having a polystyrene backbone with 2-hydroxyethyl-dimethylammoniummethyl side chains with a chloride counterion); Diaion SA20A OH (having a polystyrene backbone with 2-hydroxyethyl-dimethylammoniummethyl side chains with a hydroxide counterion; Diaion DCA11, and WA30 (each having a polystyrene backbone with a dimethylaminomethyl side chains); Diaion TSA1200 and RSA1200 (each having a polystyrene backbone with 4-(trimethylammonium)but-1-yl side chains with a hydroxide counter ion); Diaion CR20, WA20, and WA21j (each having a polystyrene backbone and a polyethyleneiminemethyl side chain); PrepEx DEAE (having a 2-diethylamino-1-hydroxyethyl side chain); Sephabeads FP-DA13 (having a diethylamino side chain); Sephabead FP-HA-13 (having a 6-aminohexylamino side chain); Diaion CRBO1, CRB02 (each having a polystyrene backbone and a 2,3,4,5,6-pentahydroxyhexyl-N-methylaminomethyl side chain); and Diaion WA10 (having a polyacrylamide backbone and a dimethylaminoalkylene side chain pendent on the acrylamide nitrogen); DIAION™ HP20, HP21, and SEPABEADS™ SP825L, SP850, SP70, SP700 or the like; modified aromatic type adsorbents such as modified styrene-divinylbenzene polymer based resins that include brominated styrene-divinylbenzene polymer based resins or any other substituted styrene-divinylbenzene polymers for example SEPABEADS™ SP207; methacrylic type resins such as DIAION™ HP2MG; Duolite XAD-761 (available from Rohn and Haas), Amberline XAD 761 (available from Rohm and Haas), Sephadex™ LH-20 or mixtures thereof.

Pore volume of the resin used in step (a) can be about 0.5 mL/g, about 0.7 mL/g, about 0.8 mL/g, about 0.9 mL/g, about 1.0 mL/g, about 1.1 mL/g, about 1.2 mL/g, about 1.3 mL/g, about 1.4 mL/g, about 1.5 mL/g, about 1.6 mL/g, about 1.7 mL/g, about 1.9 mL/g, about 2.0 mL/g, about 2.5 mL/g or any other suitable pore volume.

Surface area of the resin used in step (a) can be about 400 $m^2/g$, about 450 $m^2/g$, about 500 $m^2/g$, about 550 $m^2/g$, about 570 $m^2/g$, about 600 $m^2/g$, about 620 $m^2/g$, about 650 $m^2/g$, about 670 $m^2/g$, about 700 $m^2/g$, about 750 $m^2/g$, about 800 $m^2/g$, about 850 $m^2/g$, about 900 $m^2/g$, about 950 $m^2/g$, about 1000 $m^2/g$, about 1050 $m^2/g$, about 1100 $m^2/g$, about 1200 $m^2/g$, about 1250 $m^2/g$, about 1300 $m^2/g$ or any other suitable surface area.

Pore size/redius of the resin used in step (a) can be about 20 A, about 30 A, about 40 A, about 50 A, about 60 A, about 70 A, about 80 A, about 90 A, about 100 A, about 110 A, about 120 A, about 130 A, about 140 A, about 150 A, about 160 A, about 170 A, about 180 A, about 190 A, about 200 A, about 230 A, about 250 A, about 270 A, about 290 A, about 300 A or any other suitable pore size/redius.

Step (b) involves washing the resin loaded with the mixture of estrogens with water immiscible organic solvent.

Optionally, step (b) can be preceded or succeeded by washing the resin loaded with the mixture of estrogens with water optionally that is acidic or basic.

Suitable water immiscible solvents that can be used in step (b) include halogenated hydrocarbons such as dichloromethane, chloroform, 1,1,2-trichloroethane, 1,2-dichloroethene; aromatic hydrocarbons such as toluene, xylene, chlorobenzene; aliphatic or alicyclic hydrocarbons such as hexane, heptane, pentane, cyclohexane, methylcyclohexane; ethers such as diethyl ether, diisopropyl ether, tert-butyl methyl ether, dibutyl ether; esters such as ethyl acetate, isopropyl acetate, n-propyl acetate, isobutyl acetate, n-butyl acetate, 2-ethylhexyl acetate or mixtures thereof.

The washing of the resin loaded with the mixture of estrogens with water immiscible organic solvent in step (b) can be carried out one or more times with one or more solvents to get the desired quality. The said solvents used for the washing may be same or different for each subsequent washing after the first washing.

The resulting washings obtained after first washing in step (b) can be optionally re-circulated for one or more times through the resin loaded with estrogens or washing can be done without re-circulation i.e., washing by single passage of solvent through resin column.

Optionally, the solvent may contain an acid. Suitable acid that can be used includes inorganic acid such as hydrochloric acid, hydrobromic acid, sulfuric acid, phosphoric acid, nitric acid; organic acids such as formic acid, acetic acid, trifluoroacetic acid, chloroacetic acid, propionic acid, butanoic acid, isobutyric acid, valeric acid, isovaleric acid, benzoic acid, salicylic acid, phthalic acid, p-toluenesulphonic acid, o-toluenesuiphonic acid, benzenesulphonic acid, methanesulphonic acid, ethanesulphonic acid.

Optionally, the solvent may contain a base. Suitable base includes alkali metal or alkaline earth metal hydroxides such as sodium hydroxide, potassium hydroxide, lithium hydroxide, calcium hydroxide; carbonates such as sodium carbonate, potassium carbonate, cesium carbonate, calcium carbonate, magnesium carbonate, sodium bicarbonate, potassium bicarbonate, alkoxides such as sodium methoxide, potassium methoxide, sodium ethoxide, potassium ethoxide; amines such as ammonia, methyl amine, diethanolamine, triethylamine, diethylamine, diisopropyl ethyl amine, butylamine, cyclohexylamine, dicyclohexylamine.

The quantity of solvent that can be used in step (b) may impact the quality and yield of the mixture of estrogens. The quantity of solvent that can be used in step (b) is selected such that it is sufficient to substantially wash out the impurities such as free steroids, phenolic constituents including cresol, dihydro-3,4-bis[(3hydroxyphenyl) methyl]-2(3H)-furanone (HPMF) and other urinary impurities without significant quantity of estrogens being washed out during such washing. For example, the quantity of solvent that can be used in step (b) can be about 10 bed volumes, about 8 bed volumes, about 6 bed volumes, about 4 bed volumes or about 2 bed volumes, about 1 bed volume, about 0.5 bed volume, about 0.2 bed volume, about 0.1 bed volume or any other suitable quantity of solvent per bed volume of resin.

When the process of the present application is carried out by using resin loaded in a column, the solvent can be passed through the column containing resin loaded with a mixture of estrogens in step (b) at a flow rate of about 10 bed volumes, about 8 bed volumes, about 6 bed volumes, about 4 bed volumes or about 2 bed volumes, about 1 bed volume, about 0.5 bed volume, about 0.2 bed volume, about 0.1 bed volume per hour or any other suitable flow rate. The flow rate of solvent through the resin can be controlled by operating at a slight excess pressure or partial vacuum.

The time period for washing and/or re-circulation in step (b) may vary from few minutes to several weeks or any other suitable time period, which generally depends on the batch size and type of the resin used. For example the time period may be from about 10 minutes to about 6 weeks.

Suitable temperature that can be used in step (b) may be less than about 50° C., less than about 40° C., less than about 30° C., less than about 20° C., less than about 15° C., less than about 10° C., less than about 5° C., less than about 0° C., less than about −5° C. or any other suitable temperature.

Optionally the mixture of estrogens adsorbed on a resin in step (a) may be desorbed by eluting with an eluting liquid. The desorbed estrogens may be re-adsorbed on to a different resin for carrying out the process according to step (b) followed by step (c).

Optionally a single resin is used in both steps (a) and (b), which further makes the process simpler. That means the same resin can be used for adsorption of a mixture of estrogens on a resin according to a process in step (a) and washing can be given to the same resin loaded with a mixture of estrogens according to a process in step (b).

Step (c) involves isolating the mixture of estrogens from the resin loaded with a mixture of estrogens.

Suitable methods that can be used for the isolation in step (c) include eluting the mixture of estrogens with a solvent or slurry of the resin loaded with a mixture of estrogens with a solvent in a batch mode or any suitable methods known in the art.

Suitable solvent that can be used in step (c) includes water, $C_1$-$C_8$ linear, branched or cyclic alcohols such as methanol, ethanol, 2-nitroethanol, 2-fluoroethanol, 2,2,2-trifluoroethanol, hexafluoroisopropyl alcohol, ethylene glycol, 1-propanol, 2-propanol (isopropyl alcohol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, cyclohexanol, phenol, glycerol; $C_2$-$C_8$ ethers such as diethyl ether, diisopropyl ether, methyl t-butyl ether, glyme, diglyme, tetrahydrofuran, 2-methyltetrahydrofuran, 1,4-dioxane, dibutyl ether, dimethylfuran, 2-methoxyethanol, 2-ethoxyethanol, anisole; $C_2$-$C_8$ ketones such as acetone, ethyl methyl ketone, diethyl ketone, methyl isobutyl ketone; $C_2$-$C_8$ esters such as methyl acetate, ethyl acetate, n-propyl acetate, n-butyl acetate, isobutyl acetate, t-butyl acetate, ethyl formate, methyl propanoate, ethyl propanoate, methyl butanoate, ethyl butanoate; $C_5$-$C_8$ linear, branched or cyclic aliphatic or aromatic hydrocarbons such as n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, petroleum ethers, benzene toluene, ethylbenzene, m-xylene, o-xylene, p-xylene, trimethylbenzene, chlorobenzene, fluorobenzene, trifluorotoluene, anisole; $C_2$-$C_6$ nitriles such as acetonitrile, propionitrile, butanenitrile; halogenated hydrocarbons such as dichloromethane, 1,2-dichloroethane, trichloroethylene, perchloroethylene, 1,1,1-trichloroethane, 1,1,2-trichloroethane, chloroform, carbon tetrachloride; or mixtures thereof.

Optionally, the solvent may contain an acid. Suitable acid that can be used includes inorganic acid such as hydrochloric acid, hydrobromic acid, sulfuric acid, phosphoric acid, nitric acid; organic acids such as formic acid, acetic acid, trifluoroacetic acid, chloroacetic acid, propionic acid, butanoic acid, isobutyric acid, valeric acid, isovaleric acid, benzoic acid, salicylic acid, phthalic acid, p-toluenesulphonic acid, o-toluenesuiphonic acid, benzenesulphonic acid, methanesulphonic acid, ethanesulphonic acid.

Optionally, the solvent may contain a base. Suitable base includes alkali metal or alkaline earth metal hydroxides such as sodium hydroxide, potassium hydroxide, lithium hydroxide, calcium hydroxide; carbonates such as sodium carbonate, potassium carbonate, cesium carbonate, calcium carbonate, magnesium carbonate, sodium bicarbonate, potassium bicarbonate, alkoxides such as sodium methoxide, potassium methoxide, sodium ethoxide, potassium ethoxide; amines such as ammonia, methyl amine, diethanolamine, triethylamine, diethylamine, diisopropyl ethyl amine, butylamine, cyclohexylamine, dicyclohexylamine.

The solvent is passed through the resin in step (c) in such a way that the elution of the mixture of estrogens is substantially complete. For instance, the eluate may be re-circulated after first elution for one or more times through the resin loaded with a mixture of estrogens until the elution is substantially complete or elution can be done without re-circulation i.e., elution by single passage of solvent through resin column. Further, the solvent or mixture of solvents used for each elution in step (c) may be different from the other.

The time period for the first elution and/or re-circulation may take few minutes to several weeks or any other suitable time period, which can be easily derived by an ordinarily skilled in the art depending on the batch size and type of the resin used. For example the time period may be about 10 minutes to about 6 weeks.

The quantity of solvent that can be used in step (c) may be about 10 bed volumes, about 8 bed volumes, about 6 bed volumes, about 4 bed volumes, about 2 bed volumes, about 1 bed volume, about 0.5 bed volume, about 0.3 bed volume, about 0.2 bed volume, about 0.1 bed volume or any other suitable quantity of solvent per bed volume of resin.

When the process of the present application is carried out by using resin loaded in a column, the solvent can be passed through the column containing the resin loaded with the mixture of estrogens in step (c) at a flow rate of less than about 10 bed volumes, less than about 8 bed volumes, less than about 6 bed volumes, less than about 4 bed volumes or less than about 2 bed volumes, less than about 1 bed volume, less than about 0.5 bed volume, less than about 0.2 bed volume, less than about 0.1 bed volume per hour or any other suitable flow rate. The flow rate of solvent through the resin can be controlled by operating at a slight excess pressure or partial vacuum.

Suitable temperature that can be used in step (c) may be less than about 60° C., less than about 50° C., less than about 40° C., less than about 30° C., less than about 20° C., less than about 10° C., less than about 5° C., or any other suitable temperature.

Optionally, the eluate from the resin loaded with mixture of estrogens may be collected as a single fraction in a single container from the column being eluted or in multiple fractions in multiple containers. Optionally, multiple fractions containing varying mixtures of estrogens may be combined so as to meet the label claim of said mixture of estrogens as per USP or relevant pharmaceutical specifications.

The quantitative composition of estrogens present in the eluate or fraction is optionally determined by suitable methods known in the art, for example by High Performance Liquid Chromatography (HPLC).

Isolating the mixture of estrogens from the eluate can be effected by suitable conventional methods known in the art. In one variant, isolating the mixture of estrogens from the eluate can be effected by concentrating the eluate by suitable techniques.

Suitable techniques that can be used for concentrating the eluate include, rotational distillation using a device, such as Büchi® Rotavapor®, spray drying, agitated thin film drying, freeze drying (lyophilization); optionally under reduced pressure.

Suitable temperature that can be used for concentration of eluants may be less than about 60° C., less than about 50° C., less than about 40° C., less than about 30° C., or any other suitable temperature.

In an aspect, the mixture of estrogens prepared according to the process of the present application is in accordance with the requirements of one of USP23, USP 24, USP25, USP26, USP27 or any other relevant pharmaceutical requirement.

In another aspect, the mixture of estrogens prepared according to the process of the present application is in accordance with the requirements of the FDA Guidance for Industry Estrogens, USP-MS Method for Quantitative Characterization and Documentation of Qualitative Pharmaceutical Equivalence, dated March 2000 ("FDA Guidance").

EXAMPLES

Example 1

The Glass column (2 inch×5 foot) which contains a bottom porous filter disc was filled with SP207 resin (~3 L). The resin is tightly packed in column using water. PMU was pumped through the bottom of the column at flow rate of 0.1 to 1.0 L/min and total of 150 L of PMU pumped and elute samples were tested for estrogens by HPLC intermittently.

Yield: 12.5 g estrogens were loaded on the column.

Analytical results:

| S. No. | Component | Result |
|---|---|---|
| 1 | 17 α DHE sulfate | 6.6% |
| 2 | Equilin sulfate | 10.5% |
| 3 | Estrone sulfate | 82.9% |

Example 2

The Glass column (1 inch×1 foot) which contains a bottom porous filter disc was filled with the estrogen-loaded SP207 resin (300 mL) and the resin is allowed to settle in the column for 15 minutes. The estrogen-loaded resin column was washed with dichloromethane (3×300 mL) with a flow rate of 5 mL/min and column purged with nitrogen. Resultant resin column washed with mixture of pre-cooled tertiary butyl methyl ether (295.5 mL) and acetic acid (45 mL) with a flow rate of 5 mL/min and column purged with nitrogen. Resin column washed with tertiary butyl methyl ether (300 mL) with flow rate of 5 mL/min and purged with nitrogen. Water (300 mL) was pumped into the column at a 5 mL/min flow rate and column purged with nitrogen. Caustic solution (3×250 mL) pumped into the column at a flow rate of 5 mL/min flow rate and the column purged with nitrogen. Water (300 mL) was pumped into the column at a flow rate of 5 mL/min and column purged with nitrogen. The resultant column washed Dichloromethane (2×300 mL) at 30° C. with a flow rate of 5 mL/min and column was purged with nitrogen. Subsequently, column washed with tertiary butyl methyl ether (300 mL) at 45° C. with 5 mL/min flow rate and the column purged with nitrogen. Acetone (3×200 mL) was passed into the column at a flow rate of 5 mL/min and the eluate was collected in several fractions. Combined acetone extracts are evaporated under reduced pressure of 200 to 25 mbar and at less than 35° C. Acetonitrile (100 mL) was charged in to the concentrated mass and further subjected to evaporation at 35-45° C. under reduced pressure. Ethanol (100 mL) was added to the reaction mass and stirred for 10-15 minutes. The resultant solution evaporated completely under reduced pressure at a temperature of 35-45° C. and dried the obtained solid for 2-4 hours under reduced pressure at 35-45° C. to afford 0.249 g of the title compound.

Analytical results:

| S. No. | Component | Result |
|---|---|---|
| 1 | 17 α DHE sulfate | 3.8% |
| 2 | Equilin sulfate | 22.8% |
| 3 | Estrone sulfate | 70.9% |

Example 3

The Glass column (1 inch×1 foot) which contains a bottom porous filter disc was filled with the estrogen-loaded SP207 resin (300 mL) and the resin was allowed to settle in the column for 15 minutes. The estrogen-loaded resin column was washed with dichloromethane (3×300 mL) with a flow rate of 5 mL/min and column purged with nitrogen. Resultant resin column washed with mixture of pre-cooled tertiary butyl methyl ether (295.5 mL) and acetic acid (45 mL) with a flow rate of 5 mL/min and column purged with nitrogen. Resin column washed with tertiary butyl methyl ether (300 mL) with flow rate of 5 mL/min and purged with nitrogen. Water (300 mL) was pumped into the column at a 5 mL/min flow rate and column purged with nitrogen. Caustic solution (3×250 mL) pumped into the column at a flow rate of 5 mL/min flow rate and the column purged with nitrogen. Water (300 mL) was pumped into the column at a flow rate of 5 mL/min and column purged with nitrogen. The resultant column washed Dichloromethane (2×300 mL) at 30° C. with a flow rate of 5 mL/min and column was purged with nitrogen. Subsequently, column washed with tertiary butyl methyl ether (300 mL) at 45° C. with 5 mL/min flow rate and the column purged with nitrogen. Column was washed with toluene (2×200 mL) with 5 mL/min flow rate and column was purged with nitrogen. Column was washed with chloroform (200 mL) with 5 mL/min flow rate and the column was purged with nitrogen. Acetone (3×200 mL) was passed into the column at a flow rate of approximately 5 mL/min and the eluate was collected in several fractions. Combined acetone extracts are evaporated under reduced pressure of 200 to 25 mbar and at less than 35° C. Acetonitrile (100 mL) was charged in to the concentrated mass and further subjected to evaporation at 35-45° C. under reduced pressure. Ethanol (100 mL) was added to the reaction mass and stirred for 10-15 minutes. The resultant solution was evaporated completely under reduced pressure at a temperature of 35-45° C. and dried the obtained solid for 2-4 hours under reduced pressure at 35-45° C. to afford 0.249 g of the title compound.

Analytical results:

| S. No. | Component | Result |
|---|---|---|
| 1 | 17 α DHE sulfate | 4.0% |
| 2 | Equilin sulfate | 22.8% |
| 3 | Estrone sulfate | 70.7% |

Example 4

Estrogens form pregnant mare's urine was adsorbed on the ion exchange columns, containing an absorbent SP207 resin (40 L) and washed with water (200 L) to remove non-specifically bound (unwanted) material. Crude mixture of Estrogen from each column was desorbed separately into methanol (200 L). The methanol extract (200 L) was concentrated at below 50° C. under vacuum. The resultant mixture (8 L) washed with dichloromethane (3×8 L). Aqueous layer (~7 L) containing the product was maintained at 40° C. under vacuum for 90 minutes. Aqueous layer pH was adjusted to 6.0-8.5 with sodium hydroxide or Hydrochloric acid and washed with diethyl ether (6 L). The resulted aqueous layer pH was adjusted to 3.5-4.5 with 10% diluted hydrochloric acid −5 to 5° C. and washed with diethyl ether (6 L). Aqueous layer was heated to 40° C. and is maintained for 180 minutes under vacuum. Cooled to 0-10° C. and pH was adjusted to 13.0-14.0 using sodium hydroxide solution. Separated isolated solid was filtered, washed with n-Butanol and filtrate extracted with n-Butanol (2×6 L). Combined solid and organic layer containing n-Butanol distilled completely at below 50° C. under vacuum. The resultant solid dried for 4-6 hours at 45-50° C. under vacuum. Dry material (213.5 g) was dissolved in water (2 L) and pH was adjusted to 5.5-6.5 with 10% diluted hydrochloric acid at 0-10° C. Barium chloride solution (2 L; 30-40% w/v) was added and the separated barium estrogen salt (231.7 g) was filtered. Barium estrogen salt was dissolved in ethanol (4 L) at 50° C., sodium sulfite solution (0.58 L) was added to the ethanol solution. The precipitated solid was filtered, washed with ethanol (1×3.5 L, 1×2 L) and filtrate distilled at below 50° C. under vacuum. To the concentrated residue acetone (4 L) was added, heated to 50° C. and undissolved solid was filtered. The solid extraction in acetone was repeated for 5 times (1×4 L, 4×3 L) and total acetone filtrate distilled completely at below 50° C. under vacuum. The obtained solid was dried for 4-6 hours at 45-50° C. under vacuum to afford 30.3 g of title product.

Analytical results:

| S. No. | Component | Result |
|---|---|---|
| 1 | 17 α DHE sulfate | 12.56% |
| 2 | Equilin sulfate | 25.38% |
| 3 | Estrone sulfate | 56.74% |

Example 5

Estrogens form pregnant mare's urine was adsorbed on the ion exchange columns, containing an absorbent HP20 resin (40 L) and washed with water (200 L) to remove non-specifically bound (unwanted) material. Crude mixture of Estrogen from each column was desorbed separately into methanol (200 L). The methanol extract (200 L) was concentrated at below 50° C. under vacuum. The resultant mixture (8 L) washed with dichloromethane (3×8 L). Aqueous layer (~7 L) containing the product was maintained at 40° C. under vacuum for 90 minutes. Aqueous layer pH was adjusted to 6.0-8.5 with sodium hydroxide or Hydrochloric acid and washed with diethyl ether (6 L). The resulted aqueous layer pH was adjusted to 3.5-4.5 with 10% diluted hydrochloric acid −5 to 5° C. and washed with diethyl ether (6 L). Aqueous layer was heated to 40° C. and is maintained for 180 minutes under vacuum. Cooled to 0-10° C. and pH was adjusted to 13.0-14.0 using sodium hydroxide solution. Separated isolated solid was filtered, washed with n-Butanol and filtrate extracted with n-Butanol (2×6 L). Combined solid and organic layer containing n-Butanol distilled completely at below 50° C. under vacuum. The resultant solid dried for 4-6 hours at 45-50° C. under vacuum. Dry material (213.5 g) was dissolved in water (2 L) and pH was adjusted to 5.5-6.5 with 10% diluted hydrochloric acid at 0-10° C. Barium chloride solution (2 L; 30-40% w/v) was added and the separated barium estrogen salt (231.7 g) was filtered. Barium estrogen salt was dissolved in ethanol (4 L) at 50° C., sodium sulfite solution (0.58 L) was added to the ethanol solution. The precipitated solid was filtered, washed with ethanol (1×3.5 L, 1×2 L) and filtrate distilled at below 50° C. under vacuum. To the concentrated residue acetone (4 L) was added, heated to 50° C. and undissolved solid was filtered. The solid extraction in acetone was repeated for 5 times (1×4 L, 4×3 L) and total acetone filtrate distilled completely at below 50° C. under vacuum. The obtained solid was dried for 4-6 hours at 45-50° C. under vacuum to afford 30.3 g of title product.

Analytical results:

| S. No. | Component | Result |
| --- | --- | --- |
| 1 | 17 α DHE sulfate | 22.06% |
| 2 | Equilin sulfate | 22.45% |
| 3 | Estrone sulfate | 46.37% |

Example 6

The Glass column (1 inch×2 foot) which contains a bottom porous filter disc was filled with the estrogen-loaded SP207 (1000 mL) and the resin was allowed to settle in the column for 15 minutes. The estrogen-loaded resin column was washed with dichloromethane (3×1500 mL) with a flow rate of 200 mL/min and the column was purged with nitrogen. Acetone (1×2 L, 2×1 L) passed through column, combined acetone extracts are evaporated under reduced pressure at below 35° C. Ethanol (3 L) was added to the reaction mass and stirred for 10-15 minutes. The resultant solution was evaporated completely under reduced pressure at a temperature of 35-45° C. Tertiary butyl methyl ether (1 L) was added and evaporated completely under reduced pressure at a temperature of 35-45° C. The obtained solid was dried for 2-4 hours under reduced pressure at 35-45° C. to afford 13.8 g of the title compound.

Analytical results:

| S. No. | Component | Result |
| --- | --- | --- |
| 1 | 17 α DHE sulfate | 5.9% |
| 2 | Equilin sulfate | 24.7% |
| 3 | Estrone sulfate | 65.8% |

Example 7

The Glass column (1 inch×2 foot) which contains a bottom porous filter disc was filled with the estrogen-loaded SP207 (1000 mL) and the resin was allowed to settle in the column for 15 minutes. The estrogen-loaded resin column was washed with dichloromethane (3×1500 mL) with a flow rate of 200 mL/min and the column was purged with nitrogen. Aqueous sodium hydroxide solution (0.1 N, 1000 mL) followed by water (1000 mL) was pumped into the column at a flow rate of approximately 200 mL/min and the column was purged with nitrogen. The resultant resin column was washed with tertiary butyl methyl ether (1000 mL) with a flow rate of 200 mL/min and the column was purged with nitrogen. Acetone (3×1.5 mL) was passed into the column with flow rate of approximately 200 mL/min. The eluate was collected in several fractions and combined acetone extracts are evaporated under reduced pressure of 200 to 25 mbar at below 35° C. Acetonitrile (150 mL) was charged in to the concentrated mass, resultant reaction mass was distilled at below 45° C. under reduced pressure and dried the obtained solid for 2-4 hours under reduced pressure at 35-45° C. to afford 4.3 g of the title compound.

Analytical results:

| S. No. | Component | Result |
| --- | --- | --- |
| 1 | 17 α DHE sulfate | 4.1% |
| 2 | Equilin sulfate | 24.3% |
| 3 | Estrone sulfate | 69.4% |

Example 8

The SS column which contains a bottom porous filter disc was filled with the estrogen-loaded SP207. This resin was washed with tert butyl methyl ether (2×45 L) followed by with sodium hydroxide solution (0.2N, 45 L). The resin was washed with a 3:1 mixture of dichloromethane and Toluene (2×45 L) followed by the dichloromethane (4×45 L). Product was extracted into acetone and the resultant reaction mass distilled under vacuum. Ethanol was added (20 L) to the crude compound and the resultant solution was distilled completely to afford title compound.

Analytical results:

| S. No. | Component | Result |
| --- | --- | --- |
| 1 | 17 α DHE sulfate | 25.7% |
| 2 | Equilin sulfate | 14.0% |
| 3 | Estrone sulfate | 47.5% |

Example 9

Estrogens form pregnant mare's urine was adsorbed on the ion exchange columns, containing an absorbent SP207 resin (8.0 L) and purged with the nitrogen for 10 minutes. Column was washed with water (40 L) and purged with nitrogen for 20 minutes. Resultant column was washed with dichloromethane (1×24 L, 2×12 L) by re-circulating each lot of dichloromethane through column for 10 hours with a flow rate of 0.133 L/minute at 30° C. After completion of each lot of dichloromethane washing, column was purged with nitrogen for 30 minutes. Column was washed with tertiary butyl methyl ether (3×12 L) by re-circulating each lot of tertiary butyl methyl ether through column for 11 hours with a flow rate of 0.133 L/minute at 30° C. After completion of each lot of tertiary butyl methyl ether washing, column was purged with nitrogen for 30 minutes. Ethanol (3×12 L) was passed through column and recirculated the eluate through column for 10 hours with a flow rate of 0.133 L/minute at 30° C. After elution with ethanol, column was purged with nitrogen for 40 minutes.

Analytical results:

| S. No. | Component | Result (mg/mL) |
| --- | --- | --- |
| 1 | 17 α DHE sulfate | 0.165 |
| 2 | Equilin sulfate | 0.398 |
| 3 | Estrone sulfate | 0.384 |

Example 10

Estrogens form pregnant mare's urine was adsorbed on the ion exchange columns, containing an absorbent SP207 resin (8.0 L) and purged with the nitrogen for 10 minutes.

Column was washed with water (48 L) with a flow rate of 0.13 L/minute at 15° C. and purged with nitrogen for 60 minutes. Resultant column was washed with dichloromethane (12 L) with a flow rate of 0.13 L/minute at 28° C. After completion of dichloromethane washing, column was purged with nitrogen for 60 minutes. Column was washed with tertiary butyl methyl ether (36 L) with a flow rate of 0.13 L/minute at 28° C. After completion of tertiary butyl methyl ether washing, column was purged with nitrogen for 60 minutes. Ethanol (24 L) was passed through column with a flow rate of 0.13 L/minute at 28° C. After elution with ethanol, column was purged with nitrogen for 60 minutes. Column was washed with water (24 L) with a flow rate of 0.4 L/minute at 25° C. and purged with nitrogen for 60 minutes. The resultant solution containing Estrogens obtained after washing has the following composition.

Analytical results:

| S. No. | Component | Result (mg/mL) |
|---|---|---|
| 1 | 17 α DHE sulfate | 0.149 |
| 2 | Equilin sulfate | 0.303 |
| 3 | Estrone sulfate | 0.734 |

The invention claimed is:

1. A method for obtaining a mixture of estrogens, comprising:
   (a) loading by adsorption, a mixture of estrogens from pregnant mare's urine on a resin;
   (b) washing the resin loaded with the mixture of estrogens with water immiscible organic solvent selected from dichloromethane, tert-butyl methyl ether or mixtures thereof;
   (c) isolating the mixture of estrogens from the resin loaded with the mixture of estrogens;
   wherein the resin is selected from an ion exchange resin, a non-ionic resin, a chelate resin, synthetic adsorbents or combinations thereof.

2. The method according to claim 1, wherein the ion exchange resin is a cation exchange resin.

3. The method according to claim 1, wherein the ion exchange resin is an anion exchange resin.

4. The method according to claim 1, wherein the resin is a non-ionic resin.

5. The method according to claim 1, where in the resin is lipophilic, hydrophilic or hydrophobic in nature.

6. The method according to claim 1, wherein the resin is selected from aromatic type adsorbents, modified aromatic type adsorbents, and methacrylic type adsorbents.

7. The method according to claim 6, wherein the modified aromatic type adsorbent resin is modified styrene-divinylbenzene polymer based resin.

8. The method according to claim 7, wherein the modified styrene-divinylbenzene polymer based resin is brominated styrene-divinylbenzene polymer based resin.

9. The method according to claim 6, wherein the aromatic type absorbent resin is a divinylbenzene polymer based resin.

10. The method according to claim 1, wherein the resin loaded with the estrogens is washed with water immiscible organic solvent at a temperature of less than about 50° C.

11. The method according to claim 1, wherein the resin loaded with the estrogens is washed with water immiscible organic solvent at a temperature of less than about 40° C.

12. The method according to claim 1, wherein the resin loaded with the estrogens is washed with water immiscible organic solvent at a temperature of less than about 30° C.

13. The method according to claim 1, wherein the isolating step comprises eluting the mixture of estrogens from the resin loaded with the mixture of estrogens with a solvent and removal of the solvent from the eluate.

14. The method according claim 13, wherein the solvent is selected from alcohol, ketone, nitrile, ester, water or mixtures thereof.

15. The method according to claim 14, wherein the solvent is selected from methanol, ethanol, 1-propanol, 2-propanol, acetone, propanone, 1-butanone, 2-butanone, acetonitrile, water or mixtures thereof.

16. The method according to claim 13, wherein the solvent is removed from the eluate by rotational distillation, spray drying, thin film drying or freeze drying.

17. The method according to claim 16, wherein the solvent is removed from the eluate by thin film drying.

* * * * *